US00PP27500P2

(12) United States Plant Patent
Clark et al.

(10) Patent No.: US PP27,500 P2
(45) Date of Patent: Dec. 20, 2016

(54) COLEUS PLANT NAMED 'UF12-74-3'

(50) Latin Name: *Plectranthus scutellarioides*
Varietal Denomination: UF12-74-3

(71) Applicant: Florida Foundation Seed Producers, Inc., Marianna, FL (US)

(72) Inventors: David G. Clark, Gainesville, FL (US); Grayson M. Clark, Gainesville, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 14/545,808

(22) Filed: Jun. 22, 2015

(51) Int. Cl.
*A01H 5/02* (2006.01)

(52) U.S. Cl.
USPC ..... Plt./469

(58) Field of Classification Search
USPC ..... Plt./469
See application file for complete search history.

(56) References Cited

U.S. PATENT DOCUMENTS

PP21,585 P2 12/2010 Clark et al.
PP21,602 P2 12/2010 Clark et al.
PP23,585 P3 5/2013 Clark et al.

OTHER PUBLICATIONS

Florida Foundation Seed Invitation to negociate May 7, 2015.*
U.S. Appl. No. 14/120,608, filed Jun. 6, 2014, Clark et al.
U.S. Appl. No. 14/120,607, filed Jun. 6, 2014, Clark et al.
U.S. Appl. No. 14/545,807, filed Jun. 22, 2015, Clark et al.

* cited by examiner

*Primary Examiner* — Annette Para
(74) *Attorney, Agent, or Firm* — Dentons US LLP

(57) ABSTRACT

'UF12-74-3' is a new coleus plant distinguished by having deep green-colored leaves with novel multi-colored patterning, and desirable growth habit and late-flowering characteristics, as disclosed herein.

3 Drawing Sheets

STATEMENT REGARDING FEDERALLY SPONSORED RESEARCH

This invention was made with government support under FLA-ENH-004865 awarded by the Cooperative Research, Education, and Extension Service, USDA. The Government has certain rights in this invention.

Latin name of the genus and species of the plant claimed: *Plectranthus scutellarioides.*

Cultivar denomination: 'UF12-74-3'.

BACKGROUND OF THE INVENTION

The invention relates to a new and distinct cultivar of coleus plant named 'UF12-74-3'. 'UF12-74-3' originated from an open pollination conducted in May-November 2011 in Gainesville, Fla. between the female coleus plant 'UF11-60-23' (unpatented) and an unknown male coleus plant. A single seedling was chosen in May 2012 for further asexual propagation in Gainesville, Fla. (see FIG. 1 for pedigree).

'UF12-74-3' was first reproduced asexually by vegetative cuttings in Gainesville, Fla. and has been reproduced asexually for over two years through vegetative cuttings. 'UF12-74-3' has been found to retain its distinctive characteristics through successive asexual propagations.

'UF12-74-3' has not been made publicly available more than one year prior to the filing date of this application.

When 'UF12-74-3' is compared to the female parent 'UF11-60-23' (unpatented), 'UF12-74-3' and 'UF 11-60-23' have a similar lance-leaf foliage shape, but the color of 'UF11-60-23' foliage is chartreuse with red margins and yellow spotting. 'UF12-74-3' is a more vigorous plant with larger leaves and a growth habit that is more spreading than 'UF11-60-23'.

When 'UF12-74-3' is compared to the commercial cultivar 'Marquee™ Red Carpet' ('UF8-19-10', U.S. patent application Ser. No. 14/120,608, filed Jun. 6, 2014), plants of 'Marquee™ Red Carpet' have lance-leaf foliage that is uniformly colored red in the center with a mottled green/yellow margin. In contrast, 'UF12-74-3' plants have lance-leaf foliage that is mostly deep green with leaf centers irregularly colored with red, yellow, and cream colored spots. Both plants have a similar overall plant shape.

SUMMARY OF THE INVENTION

The following are the most outstanding and distinguishing characteristics of 'UF12-74-3' when grown under normal horticultural practices in Gainesville, Fla. 'UF12-74-3' has a combination of a novel growth habit, late season flowering, excellent heat tolerance, and a unique foliage color that is significantly different than other coleus plants. It has superior stability in foliage color in both sun and shade conditions. It has a vigorous mounded, spreading growth habit with excellent lateral branching when grown as a stock plant, providing ample vegetative propagules for producers. This plant has not been observed to set a significant number of flowers in any trial to date, and thus it is desirable for long-season performance in the landscape, as coleus plants that set seed usually experience late season leaf drop.

BRIEF DESCRIPTION OF THE DRAWINGS

This new coleus plant is illustrated by the accompanying photographs, which show the plant's form and foliage. The colors shown are as true as can be reasonably obtained by conventional photographic procedures. The photographs were taken from 3-month-old plants grown from cuttings in 1-gallon pots during October 2014-January 2015 in greenhouses in Gainesville, Fla.

DETAILED BOTANICAL DESCRIPTION

Figure 1:
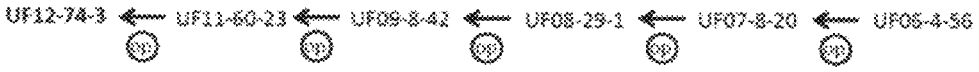
FIG. 1—shows the pedigree of the claimed plant.
Figure 2:
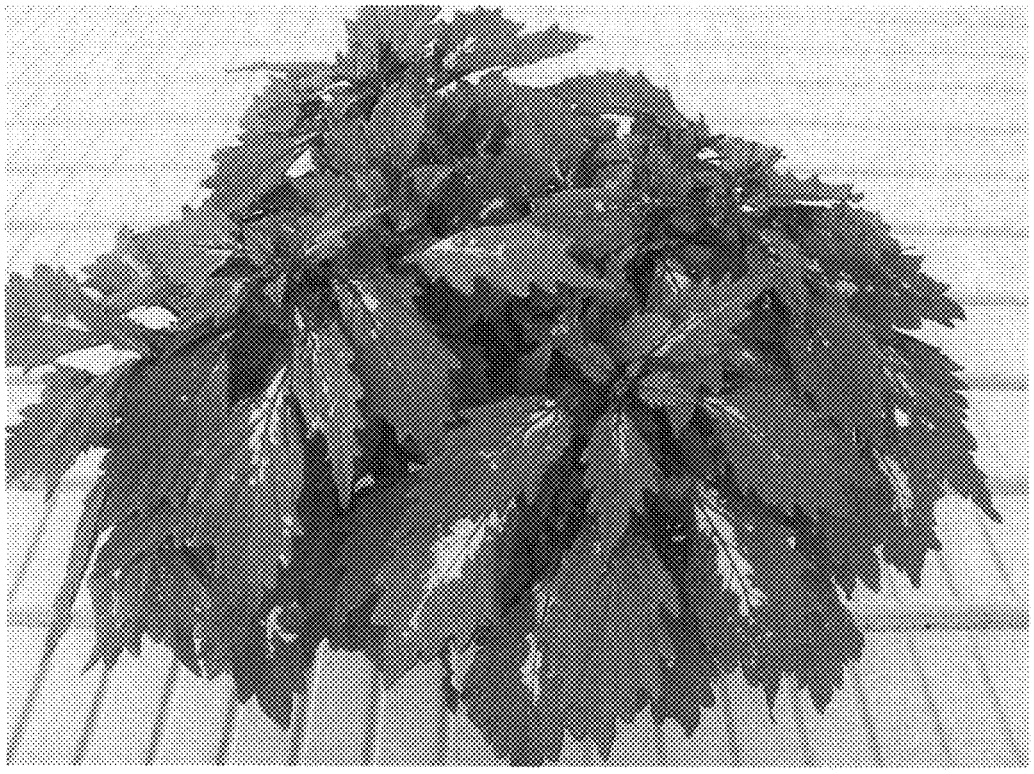
FIG. 2—shows the growth habit, form, and foliage of the claimed plant.
Figure 3:
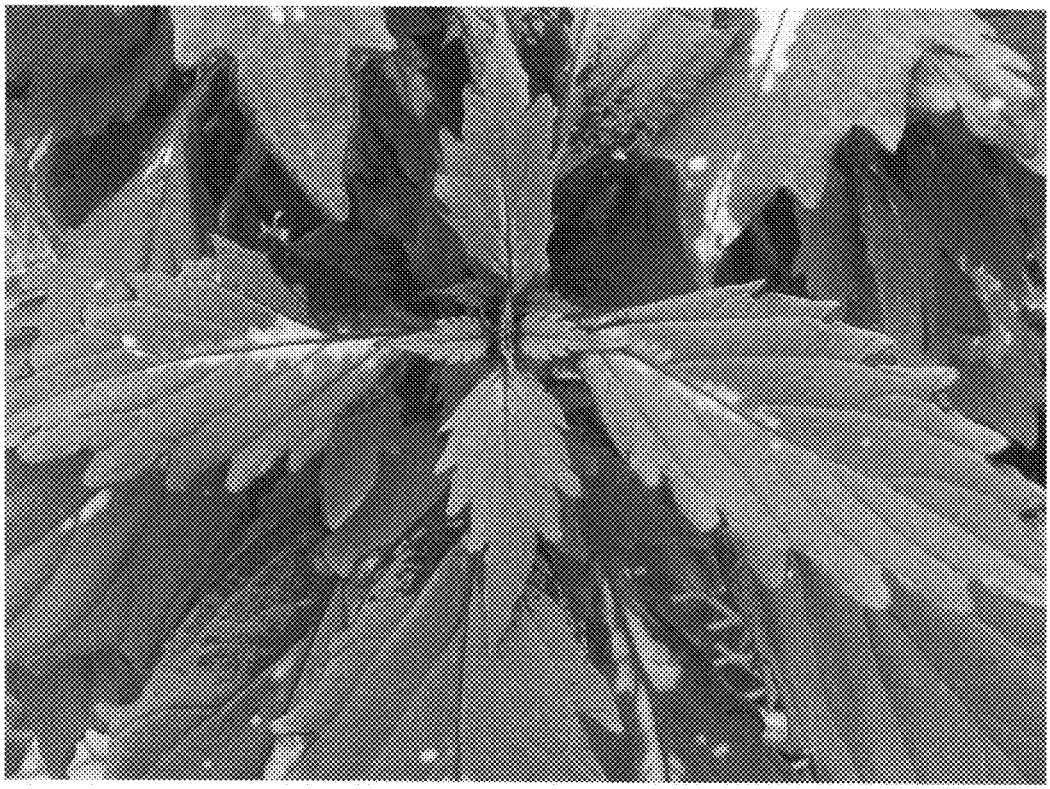
FIG. 3—shows a close-up of the foliage.

The following detailed description sets forth the distinctive characteristics of 'UF12-74-3'. The detailed description was obtained using 3-month-old plants from cuttings growing in a glass greenhouse in Gainesville, Fla., in late Fall 2014. The plants were pinched 2 weeks after cuttings were rooted, then grown in 1-gallon pots for approximately 9 weeks. Color references are to The R.H.S. Colour Chart of The Royal Horticultural Society of London (R.H.S.), 2007, 5th Edition.

Classification:

*Family*.—Lamiaceae.

*Botanical*.—*Plectranthus scutellarioides*.

*Common name*.—Coleus.

*Cultivar name*.—'UF12-74-3'.

Plant description:

*Form*.—Spreading.

*Habit*.—Upright.

*Height* (*from top of soil*).—32 cm.

*Width* (*horizontal plant diameter*).—72 cm.

Propagation:

*Type cuttings*.—Vegetative meristems having at least 1 node.

*Time to initiate roots*.—3-4 days.

*Time to produce a rooted cutting*.—7-10 days.

*Root habit*.—Fibrous.

*Root description*.—Callus forms in 2 to 3 days, roots initiate in 3-4 days and become a highly branched cutting in 7-10 days.

Branches:

*Quantity per plant*.—7 main branches per plant with numerous side branches, pinched once.

*Branch color*.—RHS N186C.

*Texture*.—Smooth.

*Pubescence*.—Not present.

*Stem description*.—Square-shaped stem, 1.5 cm in diameter at the soil line.

*Branch diameter*.—0.7 cm at the base of a 28-cm-long branch.

*Branch length*.—28 cm.

*Internode length*.—3-5 cm.

*Anthocyanin*.—RHS N186C.

Leaves:

*Quantity of leaves per branch*.—17-19.

*Arrangement*.—Opposite.

*Fragrance*.—Not fragrant.

*Shape*.—Elliptic, consistent.

*Length*.—15-17 cm.

*Width*.—7-9 cm.

*Apex*.—Broadly acuminate.

*Base*.—Oblique.

*Margin*.—Lobed.

*Leaf texture* (*both surfaces*).—Smooth upper surface, smooth lower surface.

*Pubescence color* (*both surfaces*).—N/A.

*Venation color*.—Upper surface: Lower mid-vein: RHS N79B; upper, central and side veins: RHS 138A. Lower surface: Central mid-vein: RHS N77B; side veins: RHS 138B.

*Venation pattern*.—Upper surface: Reticulate. Lower surface: Reticulate.

*Color*.—Immature leaf: Upper surface: Base: RHS 152C; tip: RHS N187A. Lower surface: RHS 138B.

*Color*.—Mature leaf: Upper surface: background: RHS 138A with irregularly distributed RHS 8A, RHS 53D, RHS N187A. Lower surface: background: RHS 138B with irregularly distributed RHS 12A.

*Petiole length*.—5-7 cm.

*Petiole diameter*.—0.2-0.3 cm.

*Petiole color*.—RHS N79A.

Flowers and seeds: Flowers and seeds have not been observed to date.

Fruit/seed set: Fruit/seed not observed.

Disease and insect resistance: Disease and insect resistance is typical of the species, thus no claims are made of any superior disease or insect resistance with this cultivar. The most common insect pests observed on this plant in Gainesville, Fla. have been long-tailed or citrus mealybugs (*Pseudococcus* sp.), which occur on older stock plant material held in the greenhouse for over 3-4 months. Impatiens Necrotic Spot Virus (*Bunyaviridae*) has also been observed in plants confined in greenhouses with mixed crops (peppers) infected with Western flower thrips (*Frankliniella occidentalis*). The most common pathogen of this species in the U.S. is downy mildew (*Pernonspora lamii*), which has been observed in stock materials grown closely together in cooler growing seasons.

What is claimed is:

1. A new and distinct *Plectranthus scutellarioides* plant named 'UF12-74-3' as described and illustrated herein.

* * * * *